US008409180B2

(12) United States Patent
Blumenkranz et al.

(10) Patent No.: US 8,409,180 B2
(45) Date of Patent: *Apr. 2, 2013

(54) PATTERNED LASER TREATMENT

(75) Inventors: Mark S. Blumenkranz, Portola Valley, CA (US); Daniel V. Palanker, Sunnyvale, CA (US); Dimitri Yellachich, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 83 days.

This patent is subject to a terminal disclaimer.

(21) Appl. No.: 12/814,023

(22) Filed: Jun. 11, 2010

(65) Prior Publication Data

US 2010/0249760 A1    Sep. 30, 2010

Related U.S. Application Data

(63) Continuation of application No. 10/745,954, filed on Dec. 24, 2003, now Pat. No. 7,766,903.

(51) Int. Cl.
*A61B 18/20* (2006.01)

(52) U.S. Cl. .................. 606/4; 606/10; 607/88

(58) Field of Classification Search .................. 606/4–6, 606/10–12, 16–18; 351/205–212; 607/88, 607/89
See application file for complete search history.

(56) References Cited

U.S. PATENT DOCUMENTS

| | | | | |
|---|---|---|---|---|
| 4,917,486 A * | 4/1990 | Raven et al. | .................. | 351/221 |
| 5,057,102 A * | 10/1991 | Tomioka et al. | .................. | 606/4 |
| 5,921,981 A * | 7/1999 | Bahmanyar et al. | .............. | 606/4 |
| 5,923,399 A * | 7/1999 | Van de Velde | ................ | 351/221 |
| 6,099,522 A * | 8/2000 | Knopp et al. | ................... | 606/10 |
| 7,146,983 B1 * | 12/2006 | Hohla et al. | .................. | 128/898 |
| 8,187,257 B2 * | 5/2012 | Lin et al. | ......................... | 606/10 |

* cited by examiner

*Primary Examiner* — Ahmed Farah
(74) *Attorney, Agent, or Firm* — Lumen Patent Firm

(57) ABSTRACT

Patterned laser treatment of the retina is provided. A visible alignment pattern having at least two separated spots is projected onto the retina. By triggering a laser subsystem, doses of laser energy are automatically provided to at least two treatment locations coincident with the alignment spots. All of the doses of laser energy may be delivered in less than about 1 second, which is a typical eye fixation time. A scanner can be used to sequentially move an alignment beam from spot to spot on the retina and to move a treatment laser beam from location to location on the retina.

29 Claims, 10 Drawing Sheets

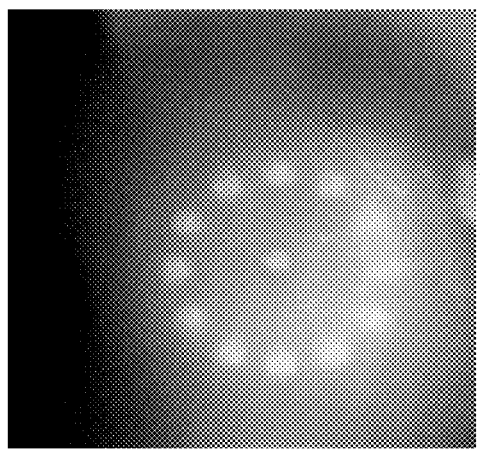 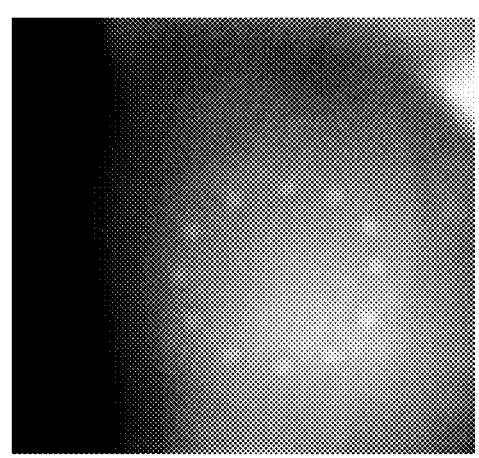
Fig. 3a                    Fig. 3b

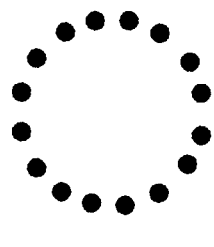
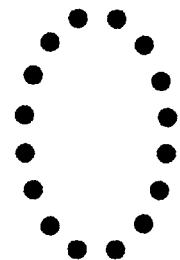
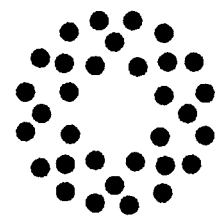
Fig. 6a    Fig. 6b    Fig. 6c
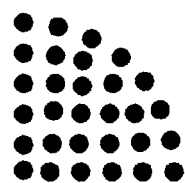
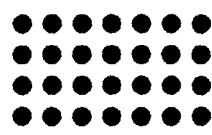
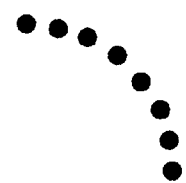
Fig. 6d    Fig. 6e    Fig. 6f
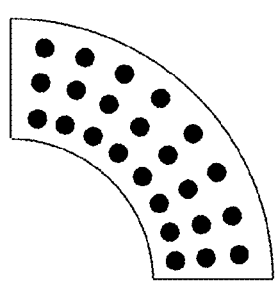
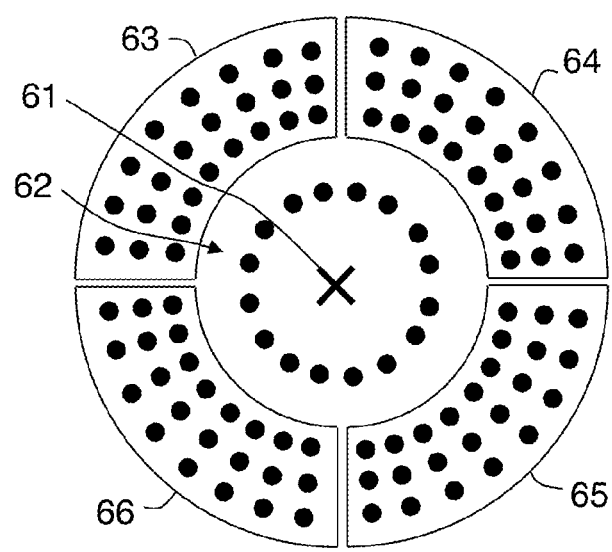
Fig. 6g
Fig. 6h

PATTERNED LASER TREATMENT

CROSS REFERENCE TO RELATED APPLICATIONS

This application is a continuation of U.S. Ser. No. 10/745,954, filed on Dec. 24, 2003, entitled "Patterned Laser Treatment of the Retina" now U.S. Pat. No. 7,766,903, and hereby incorporated by reference in its entirety.

FIELD OF THE INVENTION

The present invention relates to laser treatment of the retina, and more particularly to laser treatment of the retina at multiple locations.

BACKGROUND

Several retinal conditions, such as proliferative diabetic retinopathy, diabetic macular edema, and retinal venous occlusive diseases, respond well to retinal photocoagulation treatment. In fact, panretinal photocoagulation (PRP) is the current standard of care for proliferative diabetic retinopathy. Retinal photocoagulation procedures frequently require delivery of a large number of laser doses to the retina. For example, PRP typically requires laser treatment of at least 1500 locations. Retinal photocoagulation is typically performed point-by-point, where each individual dose is positioned and delivered by the physician. Typically, laser spots range from 50-500 microns in diameter, have pulse durations of 100-200 ms and have a beam power of 200-800 mW. Laser wavelengths are typically green, yellow or red, although occasionally infrared radiation is used. Point by point treatment of a large number of locations tends to be a lengthy procedure, which frequently results in physician fatigue and patient discomfort.

Various approaches for reducing retinal photocoagulation treatment time have been developed. Some approaches are based on taking an image of the retina to be treated, planning and aligning all treatment locations with reference to the retinal image, and treating all of these locations automatically. A tracking system is usually required in these approaches to ensure alignment between planned treatment locations defined on the image and actual treatment locations on the retina. Such tracking systems must process large amounts of data in real time, and therefore tend to be complex and difficult to implement. A representative discussion of such an approach is found in Wright et al., Journal of Biomedical Optics, 5 (1), 56-61, January 2000.

Other approaches provide multiple treatment laser beams to reduce treatment time. Multiple treatment beams can be provided by an optical beam-multiplier (e.g., U.S. Pat. No. 4,884,884 to Reis) or by an optical fiber having multiple closely spaced outputs (e.g., U.S. Pat. No. 5,921,981 to Bahmanyar et al.). Although these approaches are less complex than approaches based on retinal imaging and tracking, the treatment beam configurations cannot be easily or flexibly adjusted. For example, Reis discusses provision of a turret changer to permit selection of one beam multiplier from a set of several different beam multipliers. Such selection of one beam multiplier from a handful of beam multipliers is unlikely to provide the degree of flexibility desired in practice. Accordingly, there is a need for simple and flexible multi-location retina treatment that is not provided by known methods.

SUMMARY

It is an object of the invention to provide flexible multi-location retina treatment without the complexity of retinal image tracking. The present invention provides a system and method for patterned laser treatment of the retina. A visible alignment pattern having at least two separated spots is projected onto the retina. By triggering a laser subsystem, doses of laser energy are automatically provided to at least two treatment locations coincident with the alignment spots. Preferably, all of the doses of laser energy are delivered in less than about 1 second, which is a typical eye fixation time. In a preferred embodiment, a scanner is used to sequentially move an alignment beam from spot to spot on the retina and to move a treatment laser beam from location to location on the retina.

BRIEF DESCRIPTION OF THE DRAWINGS

FIGS. 3a and 3b are in vivo photographs showing an alignment pattern and treatment locations respectively in an animal subject.

FIGS. 6a-6h show examples of predefined patterns suitable for use with the invention.

DETAILED DESCRIPTION

Figure 1:
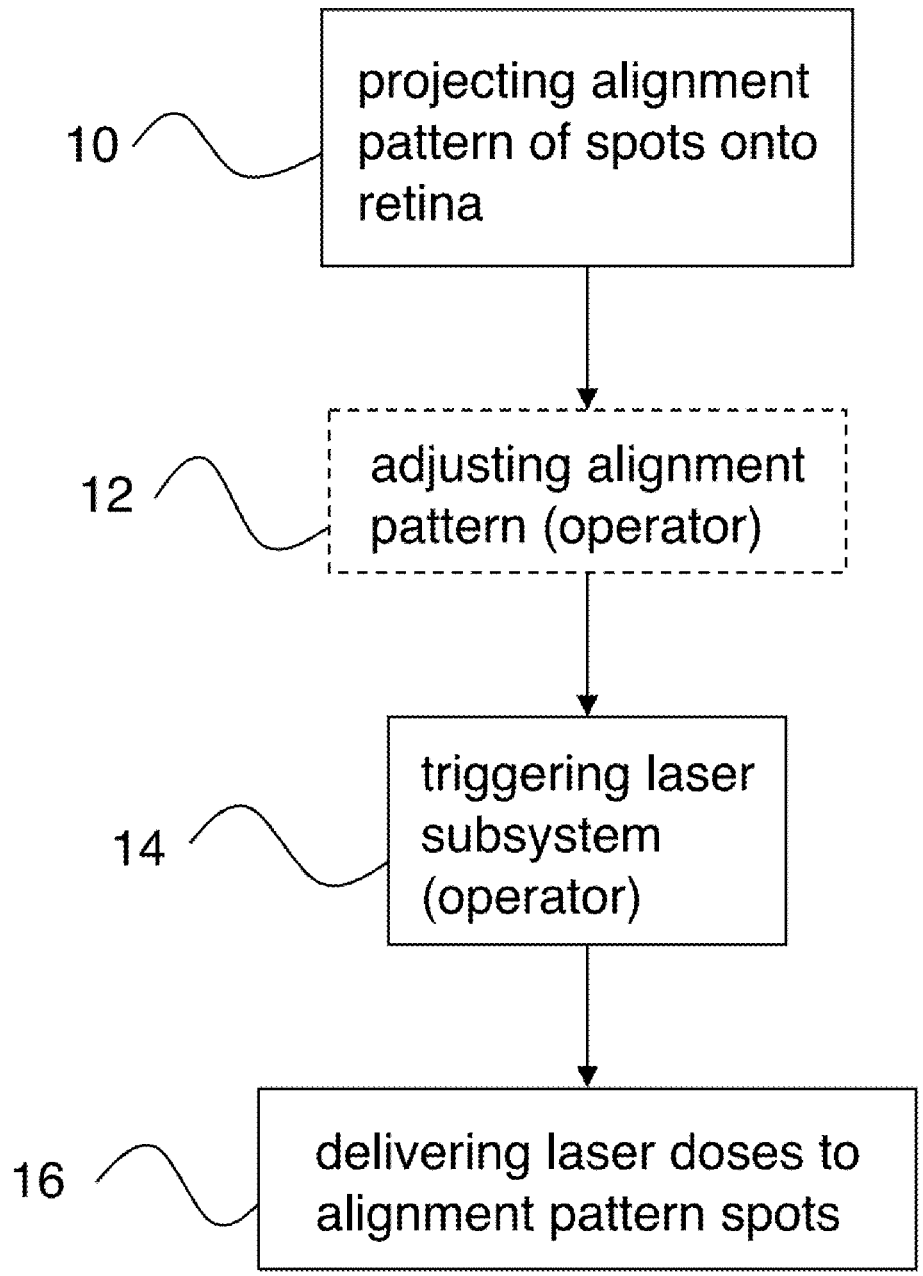
FIG. 1 is a flow diagram of a method of the present invention.

FIG. 1 is a flow diagram of a method of the present invention. A first step 10 of this method is projecting a visible alignment pattern having at least two separated spots onto a retina. In most cases, although not absolutely required to practice the invention, step 12 of adjusting the alignment pattern is performed next by an operator (e.g. a physician or a technician). This adjustment can include translation of the alignment pattern relative to the retina, in order to select areas to treat and/or to ensure that critical parts of the retina (e.g., the fovea or major blood vessels) are not treated with laser radiation. Adjustment of the pattern can also include rotation and/or scaling of the pattern, and/or changing the size of the spots to be treated.

Step 14 of triggering a laser subsystem is performed by an operator (e.g., by pressing a foot switch, pressing button, giving an audio command etc.). After step 14, step 16 is automatically performed, which entails delivering laser doses to locations on the retina which are aligned to some (or all) of the alignment pattern spots. Preferably, all of the laser doses are delivered in less than about 1 second, since 1 second is a typical eye fixation time. In this manner, doses of laser energy can be delivered to multiple locations on the retina which are aligned with spots in the alignment pattern, responsive to a single operator action. Thus, this method provides reduced treatment time for photocoagulation procedures. By delivering all the doses of laser energy in a time less than an eye fixation time, the requirement for retinal tracking is eliminated, since the eye can be expected to remain motionless during treatment. Thus, this method does not require the complexity of retinal image tracking.

An upper limit to the number of locations which can be treated in a single automatic application (or session or sequence) is obtained by dividing the maximum total treatment time by the pulse duration at each treatment location. For example, for 100 ms pulses and a maximum total treatment time of 1 second, the maximum number of treatment locations is 10. We have found that 10-50 ms pulses are preferable for practicing the invention, and 10-30 ms pulses are more preferred. The corresponding range of maximum number of locations treated in 1 second for the more preferred pulse duration range is 33-100, which is enough to provide a significant reduction in total treatment time. For example, 1500 locations can be treated using only 30 automatic applications of approximately 1 second each when each application treats 50 locations with an individual pulse duration of 20 ms.

Figure 2:
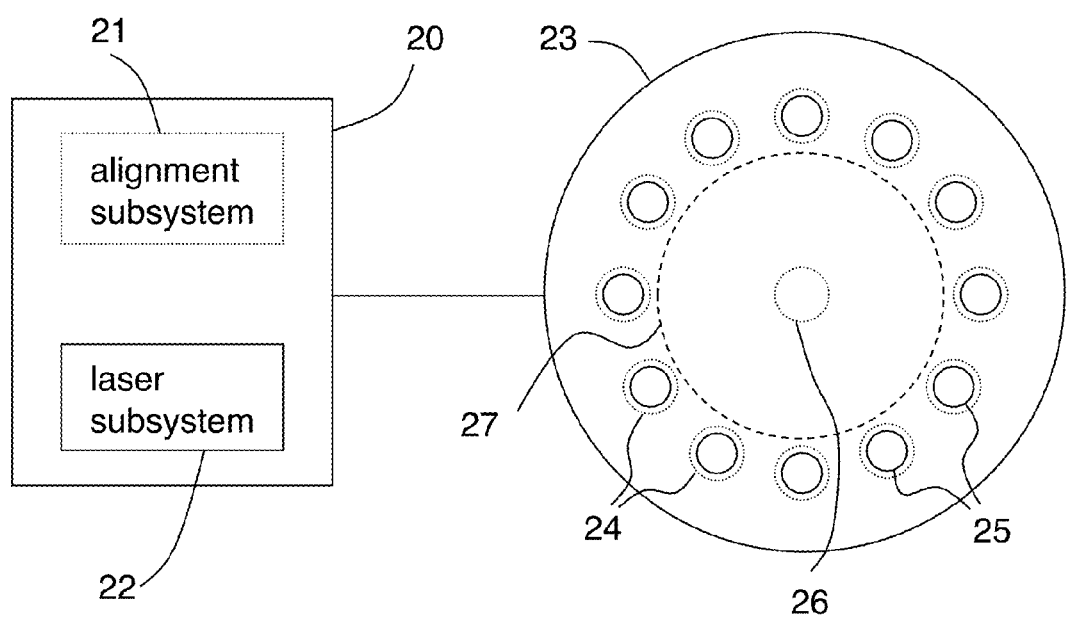
FIG. 2 shows a block diagram of an apparatus of the present invention providing an alignment pattern and treatment locations to a retina.

FIG. 2 shows a block diagram of a system 20 suitable for performing the method of FIG. 1, as well as a retina 23 having an alignment pattern and treatment locations on it. Within system 20 are two subsystems, an alignment subsystem 21 and a laser subsystem 22. Alignment subsystem 21 provides a visible alignment pattern having at least two spots to retina 23. In the example of FIG. 2, the alignment pattern has spots 24 arranged in a circle and a spot 26 at or near the center of the circle formed by spots 24. Alignment pattern spots are shown with dotted lines on FIG. 2. Laser subsystem 22 provides doses of laser energy to at least two treatment locations on retina 23 which are substantially aligned with alignment pattern spots. In the example of FIG. 2, treatment locations 25 are arranged in a circle and are substantially aligned with alignment spots 24. Treatment locations are shown with solid lines on FIG. 2. Perfect alignment of alignment spots to treatment locations is not required. For example, FIG. 2 shows treatment locations 25 which are slightly smaller than alignment spots 24. Alternatively, treatment locations 25 could be larger than alignment spots 24 and/or be slightly offset from alignment spots 24. There is no treatment location corresponding to spot 26. Therefore, spot 26 can be used as a fixation spot, for example, by aligning it to a patient's fovea and requesting the patient to fixate on spot 26.

In the example of FIG. 2, the alignment pattern has an exclusion zone 27 within which no treatment locations are disposed. Such an exclusion zone is helpful for ensuring that locations on the retina which should not be laser treated are not laser treated. For example, the exclusion zone can be aligned with the fovea so that the fovea is not treated. The exclusion zone may or may not contain alignment pattern spots. If an alignment pattern spot is present within the exclusion zone, it can be used to aid alignment of the exclusion zone by being used as a fixation spot as indicated above, or it can be aligned to a particular feature, such as a retinal tear, which should not be treated.

FIGS. 3a and 3b are photographs of an alignment pattern and treatment locations respectively from an animal test of a method according to the invention. The test shown in FIGS. 3a and 3b corresponds to the alignment pattern and treatment locations shown in FIG. 2. In particular, there is no treatment location in FIG. 3b corresponding to the central alignment spot on FIG. 3a.

Figure 4:
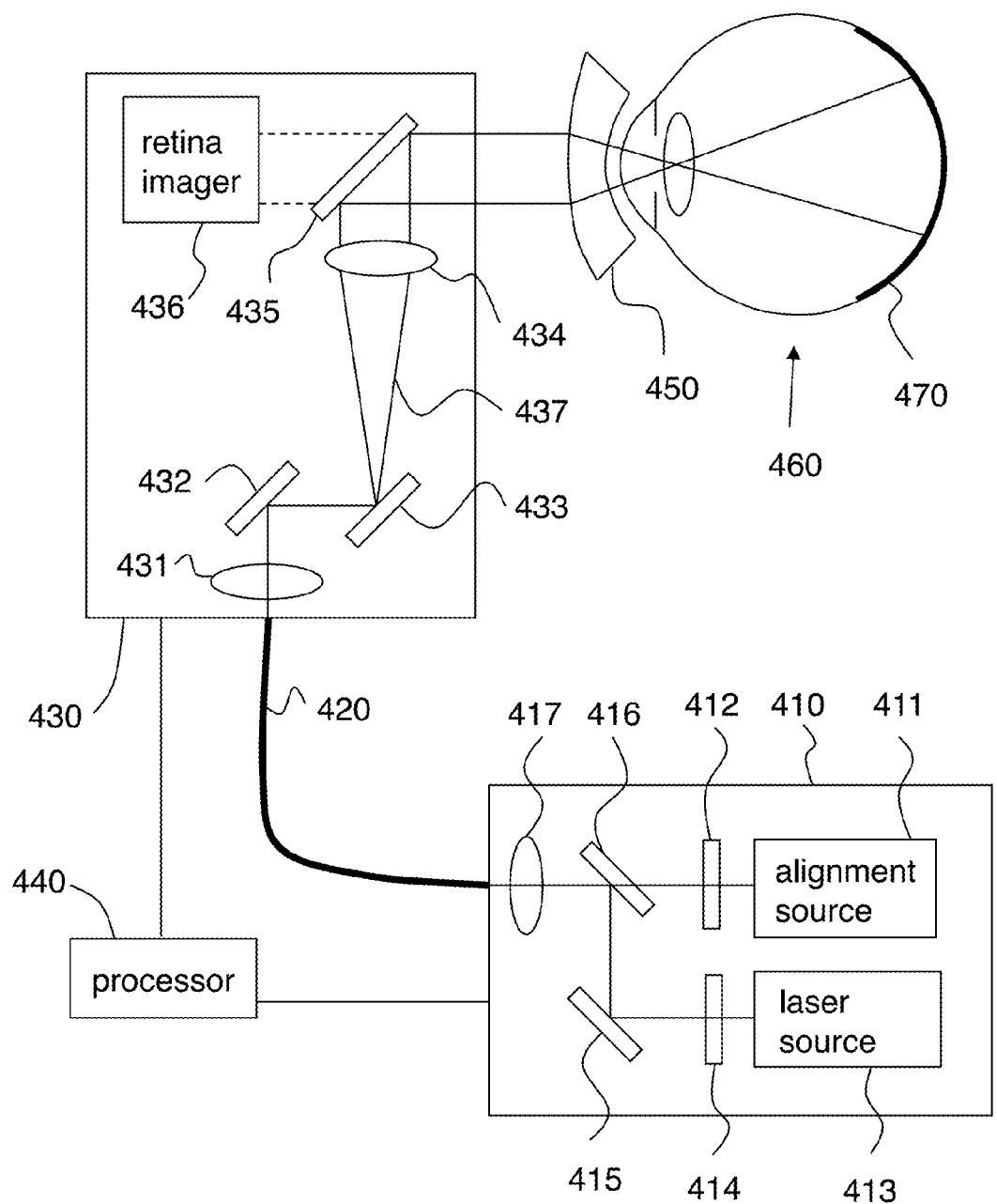
FIG. 4 shows an apparatus of an embodiment of the present invention.

FIG. 4 shows an apparatus of an embodiment of the present invention. A source module 410 is coupled by a fiber 420 to a scanner module 430. Source module 410 and scanner module 430 are controlled by a processor 440. Radiation emitted from scanner module 430 impinges on a retina 470 of an eye 460, and typically passes through an optional contact lens 450 on the way.

In the example of FIG. 4, source module 410 includes an alignment source 411 and a separate laser source 413, which is a preferred embodiment, since it increases flexibility. For example, alignment source 411 can have a wavelength selected within the visible spectrum to provide improved visibility of the alignment pattern on the retina, while laser source 413 can have a wavelength selected to provide improved treatment results. In fact, the wavelength of laser source 413 can be at a non-visible wavelength. Alignment source 411 can be an LED (Light Emitting Diode) source or a low power laser source providing less than 1 mW per alignment spot. Laser source 413 can be an Argon laser, Krypton laser, diode laser, Nd—YAG laser or any other pulsed or continuous wave laser suitable for retinal therapy. Typically, the output power of laser source 413 is from about 200 mW to about 2 W.

Laser source 413 can be a pulsed laser, which can be suitable for applications such as selective Retinal Pigment Epithelial (RPE) treatment. In this case the laser pulse duration is typically within a range of about 20 ns to 2 μs, and the laser pulse energy density is within a range of about 50 to 500 mJ/cm$^2$. The short laser pulses can be applied to each treatment location in a burst. The repetition rate of pulses in the burst can be selected by dividing the desired number of pulses by the duration of treatment in each location. For example, delivery of 50 pulses during 30 ms is provided by a repetition rate of 1.7 kHz.

An alignment shutter 412 and a laser shutter 414 are disposed in the beam paths of alignment source 411 and laser source 413 respectively. These shutters provide rapid on-off switching of the alignment and laser beams under the control of processor 440 to define the pulse duration of laser energy doses. As indicated above, we have found that 10-50 ms pulses are preferable for practicing the invention for coagulation applications, and 10-30 ms pulses are more preferred. Approaches for implementing shutters 412 and 414 include, but are not limited to, mechanical shutters, liquid crystal display (LCD) devices, and/or acousto-optic modulators (AOMs). Alternatively, shutters 412 and/or 414 can be omitted if sources 411 and/or 413 provide rapid on-off switching capability. In the example of FIG. 4, the laser and alignment beams are combined by a turning mirror 415 and a dichroic beamsplitter 416, and then coupled into fiber 420 by coupling optics 417. Of course, many other arrangements of optical components are also suitable for coupling sources 411 and 413 into fiber 420, and can be used to practice the invention.

Optical fiber 420 is preferably a highly multimode fiber (i.e., number of modes >20) at the wavelength of laser source 413 and at the wavelength of alignment source 411. A highly multimode optical fiber provides a smooth and nearly constant optical intensity distribution at its output, which is desirable for practicing the invention.

Laser and alignment light emitted from fiber 420 is received by scanner module 430. Within scanner module 430, light emitted from fiber 420 is collimated by coupling optics 431, and is then deflected by scanning elements 432 and 433. In the example of FIG. 4, scanning elements 432 and 433 each provide 1-D beam deflection, so two such elements are used to provide 2-D beam deflection. Scanning elements 432 and 433 are preferably galvanically or piezoelectrically actuated optical elements suitable for beam deflection, such as mirrors. Of course, other deflection elements and/or actuation methods can also be used to practice the invention. Deflected beams 437 pass through lens 434 and optional contact lens 450 before reaching retina 470 of eye 460. Lens 434 and optional lens 450, in combination with refractive elements of eye 460 such as its cornea and lens, provide a selected alignment and laser beam spot size at retina 470, which is typically in a range of about 50 to 500 microns.

In operation of the embodiment of FIG. 4, scanning elements 432 and 433 and shutters 412 and 414 are used to define an alignment pattern and a set of treatment locations on retina 470. For example, to create the alignment pattern shown on FIG. 2, scanning elements 432 and 433 are driven such that an alignment beam from alignment source 411 defines a pattern having spots 24 and spot 26 on retina 470. Shutter 412 is closed while this beam is moved from spot to spot. The treatment locations shown on FIG. 2 are then provided by opening shutter 414 when the alignment beam is aligned with one of spots 24, and closing shutter 414 while the alignment beam is moved from spot to spot, and while the alignment beam is aligned with fixation spot 26.

An optional retina imager 436 is preferably included in a system according to the invention, to allow the physician to observe the alignment patterns and/or treatment locations on retina 470. In the example of FIG. 4, retina imager 436 is optically coupled to retina 470 via a partially transmissive mirror 435. Partially transmissive mirror 435 is preferably highly reflective at the wavelength of laser source 413, partially reflective and partially transmissive at the wavelength of alignment source 411, and transmissive at wavelength(s) of any illumination source that may be present within retina imager 436. Of course, other methods of coupling retina imager 436 to retina 470 while permitting deflected laser and alignment beams 437 to also reach retina 470 can also be used to practice the invention.

Retina imager 436 can be a biomicroscope or slit lamp, or any other instrument for observing the retina. In some cases, the physician will look into an eyepiece of retina imager 436 to observe retina 470. In other cases, retina imager 436 will include a video display of retina 470 to make observation of retina 470 more convenient. In the preferred embodiment where alignment source 411 and laser source 413 have different wavelengths, retina imager 436 will typically include an optical wavelength selective filter at its input to block light having the wavelength of laser source 413 from entering retina imager 436, while permitting light having the wavelength of alignment source 411 to enter retina imager 436. Such a filter is particularly important when observations are performed directly by a physician.

Retina imager 436 can provide either a normal image or an inverted image, depending on its optical design. Typical simple optical imaging designs provide inverted images, and addition of an optical image inverter to such a design will provide a normal (or non-inverted image). In some cases, it is preferable for the images provided by retina imager 436 to be normal images, and in such cases, an optical image inverter can be included within retina imager 436.

Many optical elements of the embodiment of FIG. 4 belong to both the alignment subsystem (21 on FIG. 2) and to the laser subsystem (22 on FIG. 2). This commonality between the two subsystems provides co-alignment of the laser and alignment beams. In particular, fiber 420 and scanning elements 432 and 433 are common to both subsystems. This greatly simplifies the embodiment of FIG. 4 compared to an embodiment where both sources are not coupled into the same fiber, or where deflection of the alignment and laser beams is performed with two separate scanners. The flexibility of the embodiment of FIG. 4 results mainly from having two sources 411 and 413 with two independent shutters 412 and 414 respectively. The embodiment of FIG. 4 shows a preferred way of aligning the laser treatment locations to the alignment spots, namely coupling both alignment source 411 and laser source 413 into the same optical fiber 420. Other methods of co-aligning alignment subsystem 21 and laser subsystem 22 can also be used to practice the invention.

Figure 5:
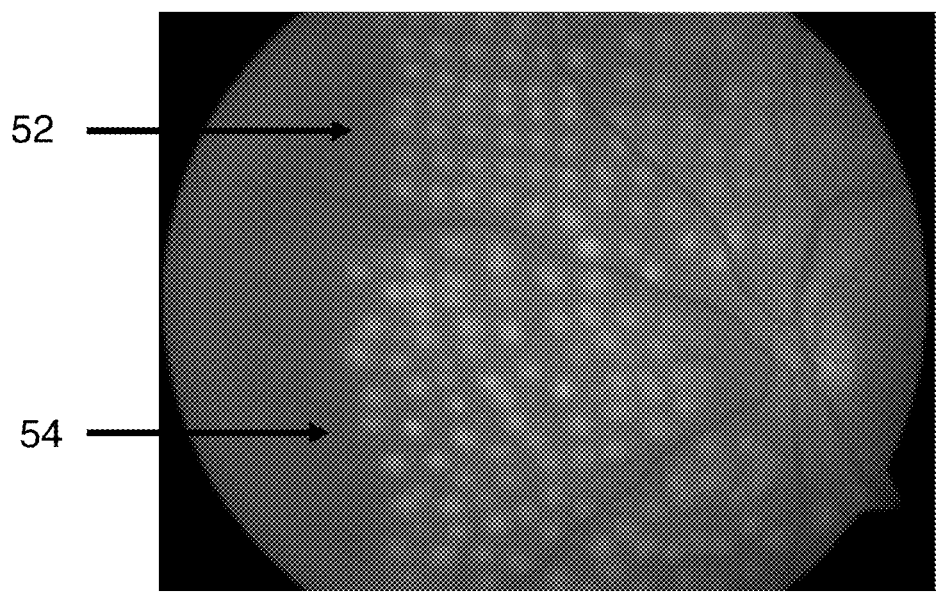
FIG. 5 is a fundus photograph comparing treatment results provided by a method of the present invention with treatment results provided by a conventional point-by-point method, in a human subject.

FIG. 5 is a photograph of retinal coagulation treatment results in a human. Treatment locations 52 were treated according to the present invention, while treatment locations 54 were treated with a conventional point-by-point technique. Clearly, treatment locations 52 are much more uniform in appearance and spacing than treatment locations 54, which demonstrates one of the principal advantages of the present invention. The photograph of FIG. 5 is a typical result from a test of a prototype of the invention on 9 patients with diabetic retinopathy. In this test, treatment time was reduced by a factor of 2.5 to 7.8. The level of pain experienced by the patients was also significantly reduced compared to conventional therapy.

Processor 440 on FIG. 4 controls source module 410 and scanner module 430. More particularly, processor 440 controls scanning elements 432 and 433, and shutters 412 and 414, to define the alignment pattern and treatment locations on retina 470. Since the alignment pattern and treatment locations are under computer control, a great deal of flexibility is provided. For example, as indicated in the discussion of FIG. 2, an alignment spot can be an untreated spot having no corresponding treatment location, which can be of benefit when planning grid photocoagulation of the macula or treatment of a peripheral tear of the retina. Such an untreated spot can also be used as a fixation spot to reduce eye motion.

The flexibility provided by the present invention can also be exploited by creating a set of predefined alignment patterns. A physician can select one or more of these predefined patterns, and adjust the orientation and/or scale of the pattern (i.e., rotate and/or magnify/demagnify the pattern), and/or translate the pattern relative to the retina, and/or change the number and/or size of the spots in the pattern, until it is appropriately aligned to a patient's retina. Thus an alignment pattern having a large number of spots in it can be aligned to a patient's retina without the physician having to deal with each alignment spot individually. A graphical user interface is a preferred approach for manipulating alignment patterns, including predefined alignment patterns. A graphical user interface is particularly convenient when used in combination with a retina imager 436 including a video display. FIGS. 6a-6h show examples of suitable predefined patterns for practicing the invention, although the invention can be practiced with any pattern. FIGS. 6a, 6b, 6d, 6d, 6e, 6f and 6g show a circular pattern, elliptical pattern, donut pattern, quadrant pattern, rectangular pattern, arc pattern and annular arc pattern respectively. Furthermore, a user-defined pattern can be created and stored for later use, and such a user-defined pattern can be used in the same way as any other predefined pattern. A database, such as described above, can be used to store user-defined patterns.

FIG. 6h shows an example of how such predefined patterns can be used in practice. In the example of FIG. 6h, feature 61 is a retinal feature, such as the macula, or a retinal tear, or a localized region of lattice degeneration, which should not be laser treated, but which should be surrounded by laser treated regions. In the case of smaller regions to be treated with a relatively limited number of total spots, typically less than 100, the entire predefined treatment pattern can be applied in less than one second. Alternatively, another method for laser treatment is to first laser treat according to a predefined circular pattern 62 encircling feature 61, and then fill in the treatment area outside circular pattern 62 using annular arc patterns 63, 64, 65, and 66. Such annular arc patterns preferably have adjustable size and orientation. The four orientations required to form a complete ring, as shown on FIG. 6*h*, are preferably predefined. Furthermore, the spot pattern of such annular arcs is preferably user-selectable. For example, FIG. 6*h* shows annular arc patterns having a 3×8 spot pattern. Other spot patterns, such as 4×6, 5×5, 6×6, 6×8, and 7×7 are also suitable for such annular arc patterns. User selection of annular arc pattern size, orientation and spot pattern is preferably accomplished with a graphical user interface, as indicated above.

Figure 7:
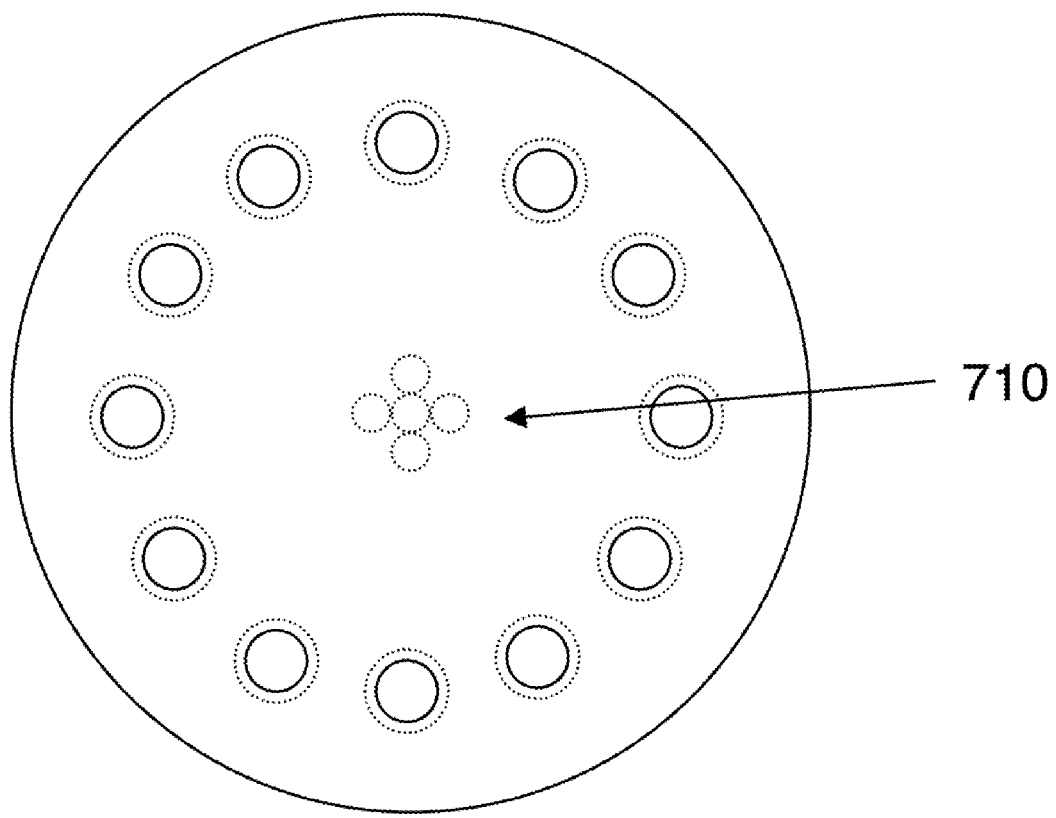
FIG. 7 shows several closely spaced fixation spots making up a fixation pattern, where the fixation pattern is not seen as circular by a patient.

A further example of the flexibility provided by the current invention is shown in FIG. 7, where several untreated alignment spots 710 are positioned next to each other to define a shape which is non-circular. In the example of FIG. 7, this shape is a + sign. When alignment spots 710 on FIG. 7 are used as fixation spots, the patient will perceive a non-circular shape, which can aid the patient in fixating on the intended fixation spot as opposed to some other spot in the alignment pattern. An alternative approach for distinguishing an untreated fixation spot from a non-fixation spot that will be treated is to scan the alignment pattern such that the fixation spot is perceived as blinking while non-fixation spots are perceived as steady (or vice versa).

Figure 8:
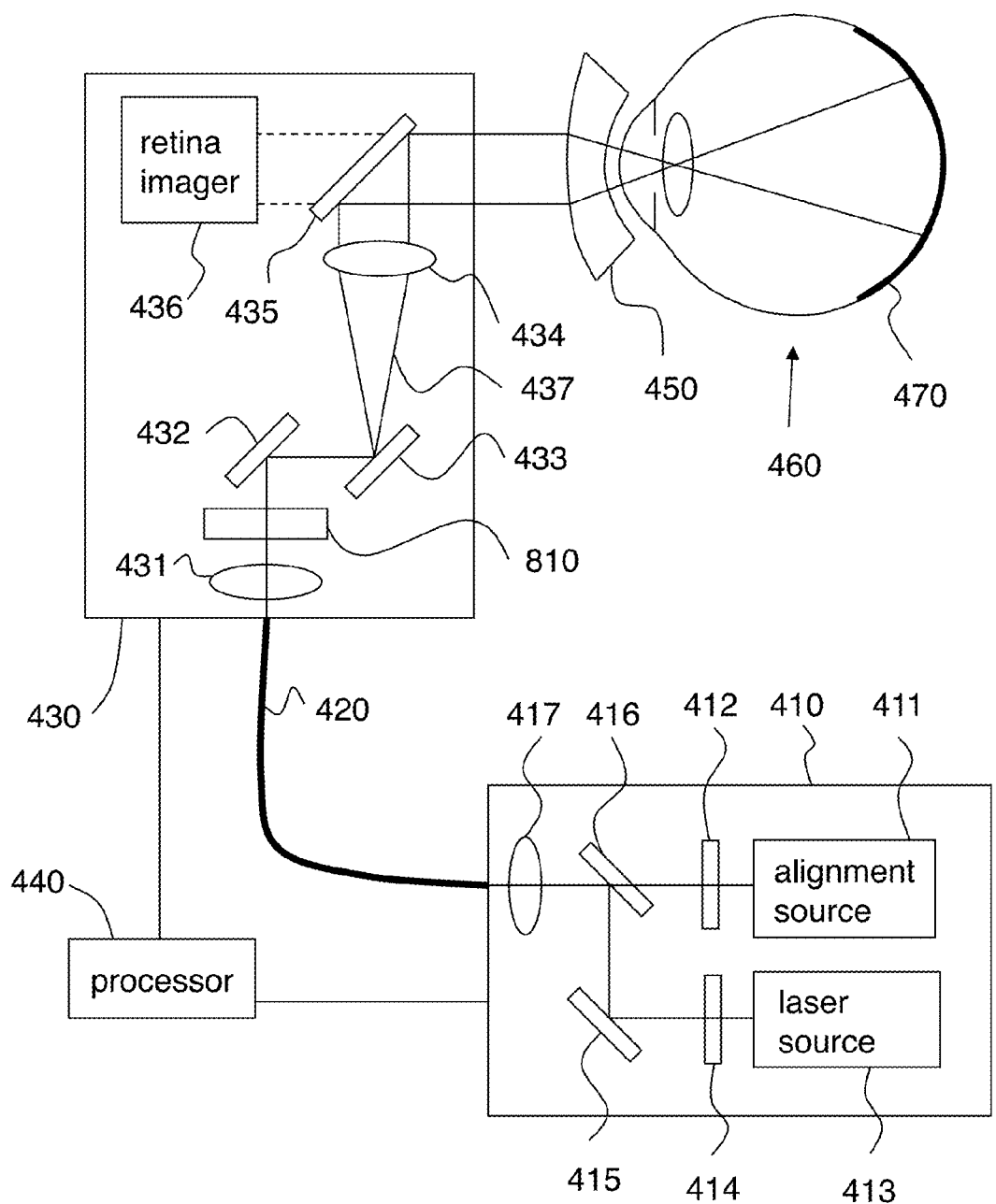
FIG. 8 shows an apparatus of an alternate embodiment of the invention having adjustment optics for changing the size of alignment and treatment beams on the retina.

Still another way to provide flexibility in the present invention is shown in the embodiment of FIG. 8, which differs from the embodiment of FIG. 4 only by insertion of adjustment optics 810 into the beam paths within scanning module 430. Adjustment optics 810, which can be an electronically controllable zoom lens, allows the spot size of the alignment and laser beams on retina 470 to be adjusted.

Figure 9:
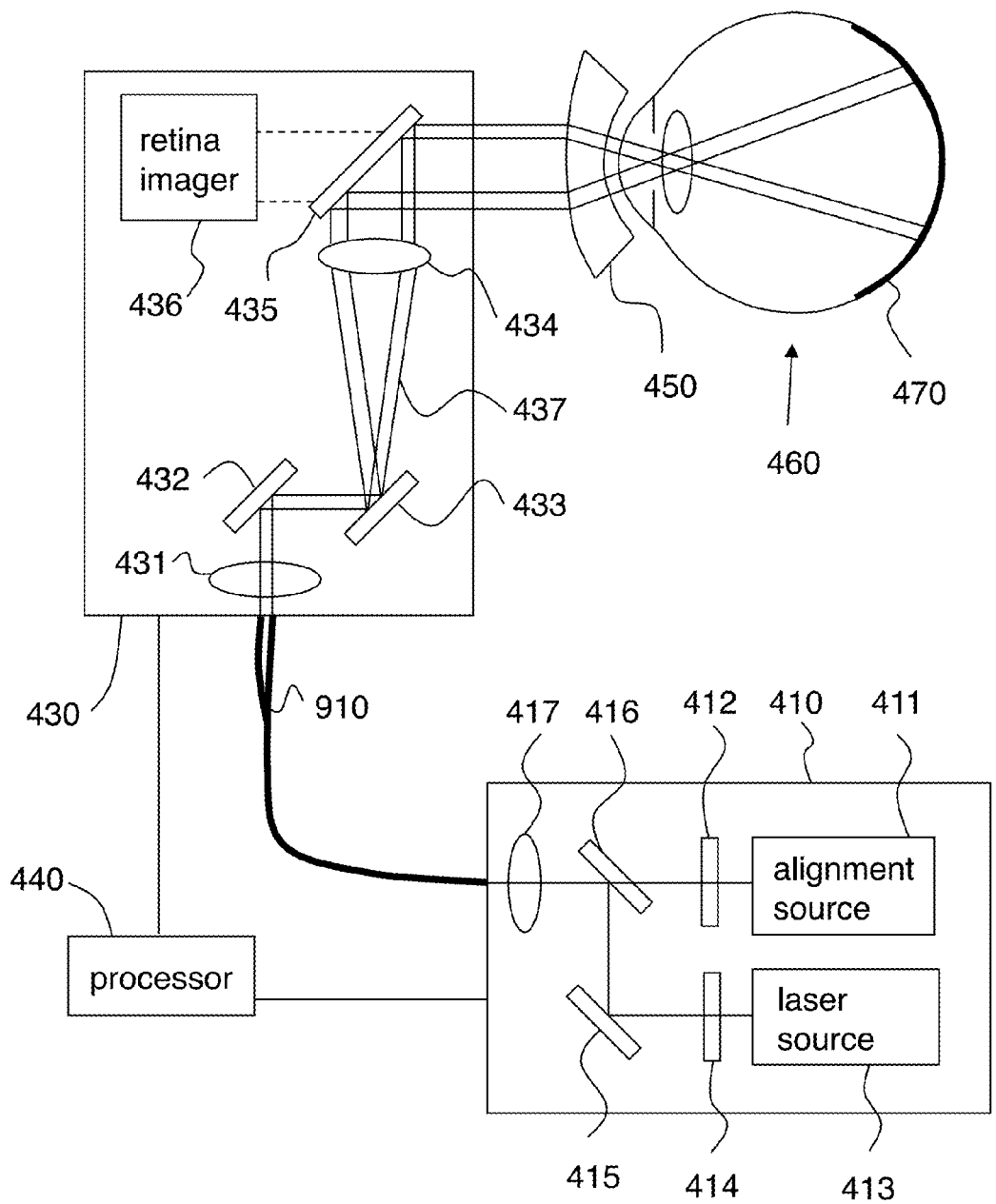
FIG. 9 shows an apparatus of an alternate embodiment of the invention having a dual-output coupling fiber.

In the embodiments of FIGS. 4 and 8, doses of laser energy are provided to the treatment locations sequentially. In some cases, it can be beneficial to provide doses of laser energy to treatment locations simultaneously. For example, the embodiment of FIG. 9 differs from the embodiment of FIG. 4 only by substitution of dual output fiber 910 for optical fiber 420 on FIG. 4. Dual output fiber 910 defines two closely spaced spots, and this pattern of two closely spaced spots can be positioned to various positions on retina 470 by scanning elements 432 and 433, as shown on FIG. 9. A benefit of this approach is that roughly twice as many spots can be treated in a given amount of time, since two doses are always provided simultaneously as opposed to only a single dose being provided at any one time. However, this approach is less flexible than scanning a single spot. For example, it is not possible to treat only one spot of a pair of spots defined by fiber 910. Also, the power from laser source 413 is split among all doses which are simultaneously delivered, so simultaneous delivery of a large number of doses will require much more power from laser source 413.

Figure 10:
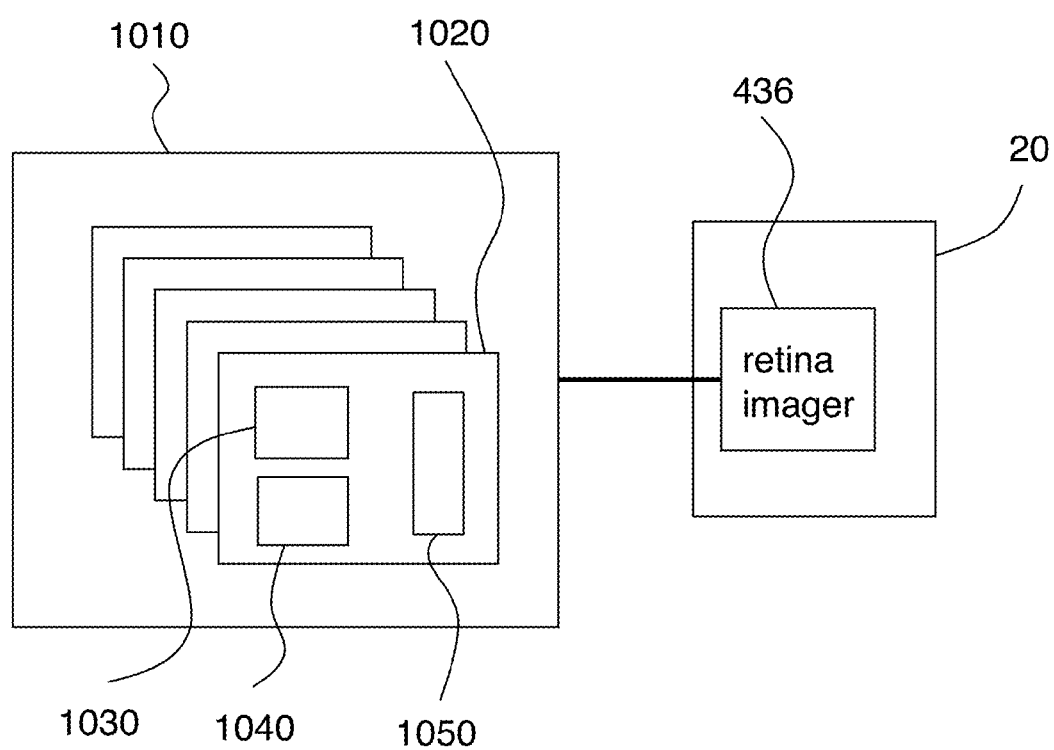
FIG. 10 shows a database suitable for recording images of alignment patterns and treatment locations according to an embodiment of the invention.

In clinical use, it will typically be preferred to include recordkeeping in a system according to the invention. As shown on FIG. 10, a database 1010 can be used to store observed images obtained from retina imager 436 of system 20. Database 1010 includes multiple records 1020, and records 1020 can include information such as images 1030 of alignment patterns, images 1040 of treatment locations, and/or patient information 1050. Images 1040 and 1050 are preferably stored in a digital format for ease of handling and access.

What is claimed is:

1. A system for laser treatment of a retina of a patient, the system comprising:
   a) a treatment source producing a treatment beam;
   b) one or more scanning elements configured to direct the treatment beam to various positions on the retina of a patient; and
   c) a processor operatively coupled to the one or more scanning elements, the processor configured to:
      1) display a visible alignment pattern that encloses a plurality of treatment locations within the visible alignment pattern; and
      2) deliver, responsive to an input from an operator and within a time period of about one second, sequential doses of laser energy to at least two of the treatment locations enclosed within the visible alignment pattern.

2. The system of claim 1, wherein the visible alignment pattern is a rectangular pattern.

3. The system of claim 1, wherein the visible alignment pattern is a circular pattern.

4. The system of claim 1, wherein the visible alignment pattern is an elliptical pattern.

5. A system for laser treatment of tissue of a patient, the system comprising:
   a. a treatment source producing a treatment beam;
   b. one or more scanning elements configured to direct the treatment beam to various positions on tissue of a patient; and
   c. a processor operatively coupled to the one or more scanning elements, the processor configured to:
      1) display a visible alignment pattern comprising a plurality of separate treatment locations on the tissue; and
      2) deliver, responsive to an input from an operator and within a time period of about one second, sequential doses of laser energy to at least two of the treatment locations.

6. The system of claim 5, wherein the treatment beam has a substantially nonvisible wavelength.

7. The system of claim 5, further comprising a multimode optical fiber configured to guide an alignment beam and the treatment beam to the one or more scanning elements.

8. The system of claim 5, wherein the tissue comprises a retina, and further comprising a retina imager configured to observe the retina.

9. The system of claim 8, wherein the retina imager comprises a biomicroscope, a slit lamp, a video display, or an optical image inverter.

10. The system of claim 8, further comprising a database configured to record observations obtained from the retina imager.

11. The system of claim 5, wherein the alignment pattern is a predefined alignment pattern.

12. The system of claim 11, wherein the predefined alignment pattern is selected from the group consisting of a quadrant pattern, a circular pattern, an elliptical pattern, a donut pattern, a rectangular pattern, an arc pattern, an annular arc pattern, and a user-defined pattern.

13. The system of claim 11, wherein the predefined alignment pattern has an adjustable scale and an adjustable orientation.

14. The system of claim 5, wherein the alignment pattern further comprises an exclusion zone, within which none of the at least two separate treatment locations is disposed.

15. The system of claim 14, wherein the tissue comprises a retina, and wherein the exclusion zone may be aligned to the fovea of the retina.

16. The system of claim 14, wherein the tissue comprises a retina, and wherein the exclusion zone may be aligned to a tear within the retina.

17. The system of claim 5, wherein the alignment pattern further comprises a fixation spot which is not aligned with any of the at least two separate treatment locations.

18. The system of claim 17, wherein the tissue comprises a retina, and wherein the fixation spot may be aligned to the fovea of the retina.

19. The system of claim 17, wherein the tissue comprises a retina, and wherein the fixation spot is configured to be perceived as blinking by the patient.

20. The system of claim 5, wherein the tissue comprises a retina, wherein the alignment pattern further comprises a plurality of fixation spots which are not aligned with any of the at least two separate treatment locations, and wherein the plurality of fixation spots is configured to be perceived as other than circular by the patient.

21. The system of claim 5, wherein the one or more scanning elements are configured to direct the treatment beam with one or more controllably actuated deflections.

22. The system of claim 21, wherein the one or more scanning elements are galvanically or piezoelectrically actuated.

23. The system of claim 21, further comprising a treatment beam shutter operatively coupled to the processor and configured to controllably block the treatment beam.

24. The system of claim 21, further comprising an alignment beam shutter operatively coupled to the processor and configured to controllably block an alignment beam that provides the alignment pattern.

25. The system of claim 24, further comprising adjustment optics configured to alter a size of the alignment beam delivered to the tissue.

26. The system of claim 5, further comprising adjustment optics configured to alter a size of the treatment beam delivered to the tissue.

27. The system of claim 5, wherein the input from the operator comprises a single triggering of the processor to controllably shutter the treatment beam.

28. The system of claim 5, wherein the doses of laser energy comprise pulses having a pulse duration between 10 ms and 50 ms.

29. The system of claim 5, wherein the doses of laser energy comprise pulses having a pulse duration of 50 ms or less.

* * * * *